United States Patent
Nakanishi et al.

(10) Patent No.: US 6,191,080 B1
(45) Date of Patent: *Feb. 20, 2001

(54) HEAT RESISTANT LUBRICATING OIL COMPOSITION

(75) Inventors: Hiroshi Nakanishi; Ko Onodera; Makoto Kanbara; Atsuhisa Kobori; Yoshinobu Nakamura, all of Ohi-machi (JP)

(73) Assignee: Tonen Corporation, Tokyo (JP)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/793,917

(22) PCT Filed: Jun. 14, 1996

(86) PCT No.: PCT/JP96/01640

§ 371 Date: Feb. 14, 1997

§ 102(e) Date: Feb. 14, 1997

(87) PCT Pub. No.: WO97/00308

PCT Pub. Date: Jan. 3, 1997

(30) Foreign Application Priority Data

Jun. 16, 1995 (JP) .................................... 7-173974

(51) Int. Cl.$^7$ ............... C10M 105/32; C10M 107/32; C10M 137/08; C10M 137/04
(52) U.S. Cl. ............ 508/437; 508/440; 508/495
(58) Field of Search ................... 508/212, 215, 508/437, 440, 495

(56) References Cited

U.S. PATENT DOCUMENTS

| | | | |
|---|---|---|---|
| 3,352,781 | * 11/1967 | Buehler . | |
| 3,677,944 | * 7/1972 | Clark . | |
| 3,714,043 | * 1/1973 | Clark . | |
| 3,748,269 | * 7/1973 | Clark . | |
| 3,751,367 | * 8/1973 | Clark | ................... 252/78.1 |
| 3,751,368 | * 8/1973 | Clark | ................... 252/78.1 |
| 3,755,178 | * 8/1973 | Clark et al. | ................... 252/78.1 |
| 3,778,472 | * 12/1973 | Clark | ............... 260/502.4 R |
| 3,832,303 | * 8/1974 | Clark . | |
| 3,843,532 | * 10/1974 | Clark . | |
| 3,844,962 | * 10/1974 | Clark . | |
| 5,344,577 | * 9/1994 | Deckman . | |

FOREIGN PATENT DOCUMENTS

WO 92/12222    7/1992 (WO) .

OTHER PUBLICATIONS

Kanbara, The third reference, Chemical Abstracts 127:83747.
European Office Action dated Jul. 24, 1998.
English Abstract of Japanese Patent Publication No. 44-8934 (8934/1964).
English Abstract of Japanese Laid-Open Patent Application No. 6-158079 (158079/1994).
Chemical Abstract 99:215225, Matveenskii, R.M. 1982.*

\* cited by examiner

*Primary Examiner*—Margaret Medley
(74) *Attorney, Agent, or Firm*—Venable; George Spencer; Marina V. Schneller

(57) ABSTRACT

A heat resistant lubricating oil composition which exhibits high heat resistance and oxidation resistance under high temperature conditions, and can withstand severe working conditions, as in jet engines or gas turbines. The lubricating oil composition comprises a polyphenylthioether of formula {I}

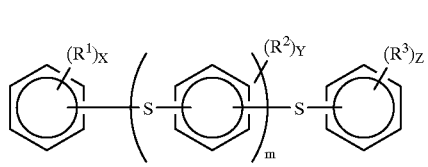

in a lubricating base oil, comprising any one of a polyol ester, dibasic acid ester, a polyphenyl ether, an organopolysiloxane and admixtures thereof.

6 Claims, No Drawings

HEAT RESISTANT LUBRICATING OIL COMPOSITION

CROSS-REFERENCE TO RELATED APPLICATION

This application is a National Stage of International Application No. PCT/JP96/01640 filed Jun. 14, 1996, designating the United States of America, the entire specification of which is incorporated herein by reference.

FIELD OF THE INVENTION

The present invention concerns a heat resistant lubricating oil composition, more in particular, it relates to a heat resistant and oxidation resistant lubricating oil composition comprising a polyphenyl thioether as an antioxidant or a lubricating base oil component and capable of withstanding use under a high temperature condition. Further, the present invention relates to a method of preventing oxidation of a heat resistant lubricating oil composition by using a polyphenyl thioether. Further, the present invention provides a production process thereof including a step of purifying a polyphenyl thioether as the constituent ingredient of a heat resistant lubricating oil composition.

DESCRIPTION OF THE PRIOR ART

In recent years, as the performance and the efficiency of machinery equipments and power equipments have become higher, conditions in the working circumstance of lubricating oils have become severer and high quality is required for lubricating oils capable of withstanding such conditions. For example, since jet engines, gas turbines and automobile engines such as turbo engines are operated at high speed and high temperature, high heat resistance and oxidation resistance are required for lubricating oils used in such engines.

Accordingly, as the lubricating oil used under conditions requiring, for example, high thermal oxidation stability, synthetic oils such as hindered ester and polyphenyl ethers have been known. For example, Japanese Patent Laid Open No.158079/1994 discloses a lubricating oil composition comprising an ester of a mixture of aliphatic acids and a hindered alcohol of 5 to 30 carbon atoms as the lubricating base oil, and phenol, amine or sulfur compound antioxidant blended therewith. Further, Japanese Patent Publication No. 8934/1969 discloses, as a lubricating base oil, a polyphenyl ether mixture comprising m-bis(phenylmercapto) benzene with other polyphenyl thioether and polyphenyl ether.

However, improvement for the heat resistance and the oxidation resistance by addition of a polyphenyl thioether to a heat resistant base oil such as a hindered ester and an organopolysiloxane has not been proposed at all. The amine or phenol antioxidant known so far has no effect in severe working conditions, for example, under high temperature conditions of higher than 200° C., involves a problem in view of the heat resistance and oxidation resistance such as causing remarkable change of viscosity, particularly, change of total acid number in a corrosive oxidation stability test and also forms a great amount of sludges, failing to provide a heat resistant lubricating oil of practical value.

SUMMARY OF THE INVENTION

In view of the situation for the development of the heat resistant lubricating oil as described above, a primary object of the present invention is to provide a heat resistant lubricating oil composition of high practical value excellent in heat resistance and oxidation resistance under severe working conditions, particularly, under a high temperature condition of higher than 200° C.

A secondary object of the present invention is to provide a heat resistant lubricating oil composition having excellent heat resistance and oxidation resistance under a high temperature condition, and improved wear resistance.

Further, a third object of the invention is to provide a method of preventing oxidation of a heat resistant lubricating oil composition.

Further, a fourth object of the present invention is to provide a production process including a step of purifying an ingredient of a heat resistant lubricating oil composition.

For solving the foregoing subjects, the present inventors, et. al have made earnest studies and found that addition of a specified polyphenyl thioether to be described later to a lubricating base oil is extremely useful for providing heat resistance and oxidation resistance under a high temperature condition and, further, a lubricating oil composition obtained by increasing the content of the polyphenyl thioether to an organic ester such as a polyol ester or a mixture of an organic ester and a polyphenyl ether or an organopolysiloxane can maintains high heat resistance and oxidation resistance under a high temperature condition and can improve the wear resistance.

It has been further found that a production process for a polyphenyl thioether excellent in the heat resistance and the oxidation resistance and improved with the weather resistance, particularly, UV-ray resistance can be provided. The present invention has been accomplished based on such findings.

Specifically, the present invention provides a heat resistant lubricating oil composition comprising:

(a) a lubricating base oil comprising an organic ester and/or an organopolysiloxane, or (b) a lubricating base oil comprising a mixture of a polyphenyl ether and an organic ester and/or an organopolysiloxane, incorporated with, from 0.05% by weight to 10% by weight, based on the total weight of the lubricating oil composition, and a polyphenyl thioether represented by the following general formula [I]:

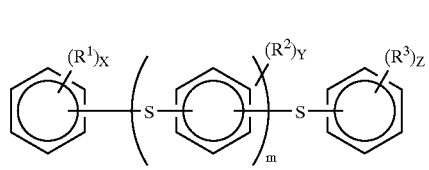

where $R^1$, $R^2$ and $R^3$ which may be identical or different with each other represent each a hydrogen atom or a hydrocarbon group of 1 to 24 carbon atoms, x, y and z which are identical or different with each other represent each an integer of 1 to 4, m is 0 or an integer of 1 to 3.

The present invention further provides a heat resistant lubricating oil composition of excellent wear resistance containing, as a lubricating base oil, from 10 to 90% by weight of (a) an organic ester and/or an organopolysiloxane, or (b) an organic ester and/or an organopolysiloxane with a polyphenyl ether, and from 90 to 10 % by weight of a polyphenyl thioether represented by the following general formula [1] described above.

The present invention further provides a method of preventing oxidation of a heat resistant lubricating oil composition under a high temperature condition, comprising adding a polyphenyl thioether and a free radical chain stopper to a synthetic lubricating base oil.

The present invention further provides a process for producing a heat resistant lubricating oil composition, which includes a step of purifying a polyphenyl thioether by applying heat treatment to a polyphenyl thioether as a component of the heat resistant lubricating oil composition under the presence of an alkali metal compound and/or an alkaline earth metal compound at a reduced pressure.

DETAILED DESCRIPTION OF PREFERRED EMBODIMENT

Then, explanation is made to the polyphenyl thioether used as the component of the heat resistant lubricating oil composition according to the present invention.

Polyphenyl thioether

The polyphenyl thioether has a structure in which aromatic rings are bonded with sulfur atoms and is represented by the following general formula [I]:

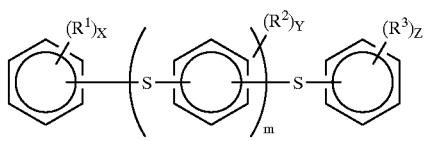

[I]

where $R^1$, $R^2$ and $R^3$ which may be identical or different with each other represent each a hydrogen atom or a hydrocarbon group of 1 to 24 carbon atoms. A compound in which all of $R^1$, $R^2$ and $R^3$ are hydrogen atoms represents polyphenyl thioether not substituted with hydrocarbon. As the hydrocarbon group, there can be mentioned, for example, a linear or branched alkyl group of 1 to 24 carbon atoms; a linear or branched alkenyl group of 2 to 24 carbon atoms, a cycloalkyl group of 6 to 24 carbon atoms; an aryl group of 6 to 24 carbon atoms. The aryl group may contain an alkyl group of 1 to 12 carbon atoms or an alkenyl group of 2 to 12 carbon atoms as a substituent. Preferred hydrocarbon group is an alkyl group of 6 to 20 carbon atoms, and those used specifically are hexyl group, heptyl group, octyl group, nonyl group, decyl group, undecyl group, dodecyl group, tridecyl group, tetradecyl group, pentadecyl group, hexadecyl group, heptadecyl group, octadecyl group, nonadecyl group and eicosyl group, and those groups mentioned above and having branchings. Those having 8 to 18 carbon atoms are particularly preferred. The hydrocarbon group may be bonded at any position of the aromatic ring.

In the general formula [I], x, y and z which may be identical or different with each other represent each an integer of 1 to 4.

In the general formula [I], m is 0 or an integer of 1 to 3, and the polyphenyl thioether in the present invention includes compounds containing 2 to 5 aromatic rings.

The thioether bond in the polyphenyl thioether may be present at any position of the aromatic rings, but those having the thioether bonds at the meta position are preferred in view of maintenance for the flowability.

Accordingly, as the polyphenyl thioether represented by the general formula [I], both the polyphenyl thioether not substituted with the hydrocarbon group and polyphenyl thioether substituted with the hydrocarbon group can be used.

The polyphenyl thioether not substituted with the hydrocarbon group is represented by the following general formula [II]:

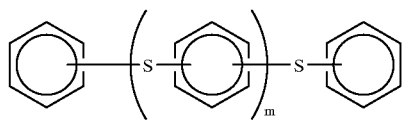

[II]

where m is 0 or an integer of 1 to 3. This is a particularly preferred compound in the present invention in view of the improvement for the heat resistance, oxidation resistance and wear resistance, as well as control for other physical properties such as the viscosity of the lubricating oil composition.

The polyphenyl thioether not substituted with the hydrocarbon group is specifically represented as below.

That is, there can be mentioned, for example,
diphenyl thioether (2P1T), m-bis(phenylmercapto)benzene (m-3P2T),
o-bis(phenylmercapto)benzene (o-3P2T),
p-bis(phenylmercapto)benzene (p-3P2T),
bis(phenylmercapto)benzene isomer mixture (mix-3P2T),
bis(m-phenylmercaptophenyl)sulfide (mm-4P3T),
bis(o-phenylmercaptophenyl)sulfide (oo-4P3T),
bis(p-phenylmercaptophenyl)sulfide (pp-4P3T),
m-phenylmercaptophenyl p-phenylmercaptophenyl sulfide (mp-4P3T),
m-phenylmercaptophenyl o-phenylmercaptophenyl sulfide (mo-4P3T),
p-phenylmercaptophenyl o-phenylmercaptophenyl sulfide (po-4P3T),
bis(mix- phenylmercaptophenyl) sulfide isomer mixture (mix-4P3T),
bis(m-phenylmercaptophenylmercapto)benzene (mmm-5P4T)
1-(m-phenylmercaptophenylmercapto)-3-(p-phenylmercaptophenylmercapto) benzene (mmp-5P4T),
p-bis(m-phenylmecarcaptophenylmercapto)benzene (mpm-5P4T)
1-(m-phenylmercaptophenylmercapto)-4-(p-phenylmercaptophenylmercapto) benzene (mpp-5P4T),
m-bis(p-phenylmercaptophenylmercapto)benzene (pmp-5P4T),
p-bis(p-phenylmercaptophenylmercapto)benzene (ppp-5P4T),
o-bis(m-phenylmercaptophenylmercapto)benzene (mom5P4T),
m-bis(o-phenylmercaptophenylmercapto)benzene (omo-5P4T),
p-bis(o-phenylmercaptophenylmercapto)benzene (opo-5P4T),
o-bis(o-phenylmercaptophenylmercapto)benzene (ooo-5P4T) and
mix-bis(phenylmercaptophenylmercapto)benzene isomer mixture (mix-5P4T).

Further, as specific examples of the polyphenyl thioether substituted with the hydrocarbon group, there can be mentioned mono-, di- or tri-alkylated polyphenyl thioether obtained by bonding 1 to 3 alkyl groups of 6 to 20 carbon atoms, preferably 10 to 17 carbon atoms as described above in the molecule can be mentioned. For example, there can be mentioned monoalkylated m-bis(phenylmercapto)benzene ($R_1$-m-3P2T), dialkylated m-bis(phenylmercapto)benzene ($R_2$-m-3P2T), trialkylated m-bis(phenylmercapto)benzene ($R_3$-m-3P2T), as well as an alkylation product of bis(m-phenylmercaptophenyl)sulfide and m-bis(m-phenylmercaptophenylmercapto)benzene.

One or more of the polyphenyl thioether not substituted with the hydrocarbon group and the polyphenyl thioether substituted with hydrocarbon group described above can be used in order to maintain low flowability.

Among the compounds exemplified above, m-bis (phenylmercapto)benzene(m-3P2T),o-bis(phenyl mercapto) benzene(o-3P2T),p-bis(phenylmercapto)benzene(p-3P2T), bis(m-phenylmercaptophenyl)sulfide(mm-4P3T) and m-bis (m-phenylmercaptophenylmercapto)benzene(mmm-5P4T) as the polyphenyl thioether not substituted with the hydrocarbon group are particularly useful for the lubricating oil composition according to the present invention in view of the improvement for the heat resistance and oxidation resistance, wear resistance and physical properties of the synthetic lubricating oil composition.

In the present invention, the polyphenyl thioether is effective as an antioxidant under a high temperature condition, which is supposed to function as a peroxide decomposer under the presence of a synthetic lubricating base oil. Particularly, it has been found according to the study of the present inventors, et. al. that when the polyphenyl thioether is added to the heat resistant base oil such as the organic ester, especially the polyol ester, it shows an extremely high heat resistance and oxidation resistance under a high temperature condition, for example, higher than 200° C. by interaction between the free radical chain stopper type antioxidant and the organic ester.

Lubricating base oil

As the lubricating base oil used for the component of the heat resistant lubricating oil composition according to the present invention, synthetic oils can be used. As the synthetic oil, organic ester including polyol ester and dibasic acid ester, polyphenyl ether, organopolysiloxane (silicone oil), as well as poly-α-olefin oil, alkylated aromatic compound and polyalkylene glycol compound can be used. The dibasic acid ester includes an adipate, azelate, sebacate, 1,9-nonamethylene dicarboxylic acid ester and so on. A complex ester can be used. As an alcohol for the dibasic acid ester, a linear or branched, a mono-or polyhydric aliphatic alcohol having 4 to 20 carbon atoms can be adopted. Those having 8 to 14 carbon atoms are preferred. As the organic ester, polyol ester is preferably used. Among all, polyol ester, polyphenyl ether and organopolysiloxane can provide high heat resistance and oxidation resistance under a high temperature condition due to interaction with the polyphenyl thioether. Particularly, a lubricating base oil comprising the polyol ester is particularly preferred. Further, a lubricating base oil comprising a mixture of a polyol ester and a polyphenyl ether, a mixture of a polyol ester and an organosiloxane and a mixture of a polyol ester, a polyphenyl ether and an organopolysiloxane is suitable and can provide a remarkable effect to the heat resistance and oxidation resistance.

Polyol ester, polyphenyl ether and organopolysiloxane are to be explained next.

Polyol ester

As the polyol ester, esters of hindered alcohols having 5 to 30 carbon atoms and aliphatic acids are used. As the hindered alcohols, there can be mentioned, for example, neopentyl glycol, 2,2-diethyl propane-1,3-diol, 2,2-dibutyl propane-1,3-diol, 2-methyl-2-propyl propane-1,3-diol, 2-ethyl-2-butyl propane-1,3-diol, trimethylol ethane, trimethylol propane, ditrimethylol propane, tritrimethylol propane, tetratrimethylol propane, pentaerythritol, dipentaerythritol, tripentaerythritol, tetrapentaerythritol, and pentapentaerythritol, and one or two or more of them are used. Preferred hindered alcohols are those having 5 to 10 carbon atoms and particularly preferred are trimethylol propane, ditrimethylol propane, pentaerythritol, dipentaerythritol, and tripentaerythritol.

As the aliphatic acid, linear or branched aliphatic acid of 4 to 10 carbon atoms are used. As the linear aliphatic acid, there can be mentioned, for example, n-butanoic acid, n-pentanoic acid, n-hexanoic acid, n-heptanoic acid, n-octanoic acid, n-nonanoic acid, and n-decanoic acid and one or more of them is used. Further, as the branched aliphatic acid, there can be mentioned, for example, 2-methyl propanoic acid, 2-methyl butanoic acid, 3-methyl butanoic acid, 2,2-dimethyl propanoic acid, 2-ethyl butanoic acid, 2,2-dimethyl butanoic acid, 2,3-dimethyl butanoic acid, 2-ethyl pentanoic acid, 2,2-dimethyl pentanoic acid, 2-ethyl-2-methyl butanoic acid, 3-methyl hexanoic acid, 2-methyl heptanoic acid, 2-ethyl hexanoic acid, 2-propyl pentanoic acid, 2,2-dimethyl hexanoic acid, 2-ethyl-2-methyl pentanoic acid, 2-methyl octanoic acid, 2,2-dimethyl heptanoic acid, 2-ethyl heptanoic acid, 2-methyl nonanoic acid, 2,2-dimethyl octanoic acid, 2-methyl nonanoic acid and 2-ethyl octanoic acid, and one or more of them are used. Preferred aliphatic acids are those having 4 to 10 carbon atoms and, particularly preferred are those having 4 to 6 carbon atoms.

For the polyol ester, production process employed so far can be used, for example, (a) a process of directly esterifying a polyol and an aliphatic acid without using a catalyst or under the presence of an acidic catalyst by way of dehydrating condensation, (b) a method of preparing an aliphatic acid chloride which is then reacted with a polyol and (c) an ester exchanging reaction between an ester of a lower alcohol and an aliphatic acid with a polyol.

Specific examples of the polyol ester in the present invention are exemplified as below (hereinafter, it is simply referred to for neopentyl glycol as NPG, trimethylol propane as TMP, ditrimethylol propane as DTMP, pentaerythritol as PE, dipentaerythritol as DPE, and tripentaerythritol as TPE).

That is, there can be mentioned NPG-di(n-butanoate), NPG-di(2-methylpropanoate), NPG-di(n-pentanoate), NPG-di(2-methylbutanoate), NPG-di(n-hexanoate), NPG-di(2-ethylbutanoate), NPG-di(3-ethylbutanoate), NPG-di(n-heptanoate), NPG-di(2-ethylpentanoate), NPG-di(n-octanoate), NPG-di(2-ethylhexanoate), NPG-di(n-nonanate), NPG-di(isononanate), NPG-di(n-decanoate), NPG-di(mixed(n-hexanoate, n-butanoate)), NPG-di(mixed (n-hexanoate, n-pentanoate), NPG-di(mixed(n-butanoate, n-heptanoate)), TMP-tri(n-butanoate), TMP-tri(2-methylpropanoate), TMP-tri(n-pentanoate), TMP-tri(2-methylbutanoate), TMP-tri(n-hexanoate), TMP-tri(3-ethylbutanoate), TMP-tri(n-heptanoate), TMP-tri(2-ethylpentanoate), TMP-tri(n-octanoate), TMP-tri(2-ethylhexanoate), TMP-tri(n-nonanate), TMP-tri (isononanate), TMP-tri(n-decanoate), TMP-tri (isodecanoate), TMP-tri(mixed(n-butanoate,n-hexanoate)), DTMP-tetra(n-butanoate), DTMP-tetra(2-methylpropanoate), DTMP-tetra(n-pentanoate), DTMP-tetra(2-methylbutanoate), DTMP-tetra(n-hexanoate), DTMP-tetra(3-ethylbutanoate), DTMP-tetra(n-heptanoate), DTMP-tetra(2-ethylhexanoate), DTMP-tetra(n-octanoate), DTMP-tetra(2-ethylhexanoate), DTMP-tetra(n-nonanate), DTMP-tetra(isononanate), DTMP-tetra(n-decanoate), DTMP-tetra(isodecanoate), DTMP-tetra[mixed(n-butanoate, n-hexanoate)], DTMP-tetra[mixed(n-pentanoate, isohexanoate)], PE-tetra(n-butanoate), PE-tetra(2-methylpropanoate), PE-tetra(n-pentanoate), PE-tetra(2-methylbutanoate), PE-tetra(2,2-dimethylpropanoate), PE-tetra(n-hexanoate), PE-tetra(2-ethylbutanoate), PE-tetra (2,2-dimethylbutanoate), PE-tetra(n-heptanoate), PE-tetra(2-ethylpentanoate), PE-tetra(n-octanoate), PE-tetra(2-ethylhexanoate), PE-tetra(n-nonanate), PE-tetra(isononanate), PE-tetra(n-decanoate), PE-tetra(isodecanoate), PE-tetra(n-decanoate), PE-tetra(isodecanoate), PE-tetra[mixed(n-pentanoate, isopentanoate,n-hexanoate, n-butanoate)], PE-tetra[mixed(n-pentanoate, isopentanoate, n-heptanoate,n-nonanate)], DPE-hexa(n-butanoate), DPE-hexa(2-methylpropanoate), DPE-hexa(n-pentanoate), DPE-hexa(2-methylbutanoate), DPE-hexa(3-m ethylbutanoate), DPE-hexa(2,2-dimethylpropanoate), DPE-hexa(n-hexanoate), DPE-hexa(2-ethylbutanoate), DPE-hexa(2,2-dimethylbutanoate), DPE-hexa(n-heptanoate), DPE-hexa(2-ethylpentanoate), DPE-hexa(n-octanoate), DPE-hexa(2-ethylhexanoate), DPE-hexa(n-nonanate), DPE-hexa(isononanate), DPE-hexa(n-decanoate), DPE-hexa[mixed(n-pentanoate, isopentanoate, n-heptanoate, n-nonanate)], TPE-octa(n-butanoate), TPE-octa(2-methylpropanoate), TPE-octa(n-pentanoate), TPE-octa(2-methylbutanoate), TPE-octa(2,2-dimethylpropanoate), TPE-octa(n-hexanoate), TPE-octa(2-ethylbutanoate), TPE-octa(n-octanoate), TPE-tetra(2-ethylhexanoate), TPE-octa(n-nonanate), TPE-octa(isononanate), TPE-octa(n-decanoate), TPE-octa[mixed(n-pentanoate,isopentanoate,hexanoate, n-butanoate)], TPE-octa[mixed(isopentanoate, n-hexanoate)], TPE-octa[mixed(n-pentanoate,isopentanoate,n-heptanoate,n-nonanate)] as well as esters of PE and a mixture containing linear and branched aliphatic acids of 4 to 10 carbon atoms. As the polyol ester in the present invention, an ester of pentaerythritol and an aliphatic acid of 4 to 12 carbon atoms is preferred, and an ester of pentaerythritol and an aliphatic acid of 4 to 6 carbon atoms, that is, PE tetra(n-butanoate), PE tetra-(n-pentanoate), PE tetra(n-hexanoate) are particularly preferred.

Polyphenyl ether

The polyphenyl ether used as the component for the base oil of the heat resistant lubricating oil composition according to the present invention has a structure in which aromatic rings are bonded with oxygen atoms and those having 3 to 6 aromatic rings in the molecule are preferred. Specifically, there can be mentioned, for example,
m-diphenoxybenzene (m-3P2E),
bis(m-phenoxyphenyl)ether (mm-4P3E),
m-phenoxyphenyl p-phenoxyphenyl ether (mp-4P3E),
m-phenoxyphenyl o-phenoxyphenyl ether (mo-4P3E),
bis(p-phenoxyphenyl) ether (pp-4P3E),
p-phenoxyphenyl o-phenoxyphenyl ether (p,o-4P3E),
bis(o-phenoxyphenyl ether (oo-4P3E),
bis(phenoxyphenyl) ether isomer mixture (mix-4P3E),
m-phenoxyphenoxy m-biphenyl (mm-4P2E),
m-bis(m-phenoxyphenoxy)benzene (mmm-5P4E),
1-(m-phenoxyphenoxy)-3-(p-phenoxyphenoxy)benzene (mmp-5P4E),
p-bis(m-pohenoxyphenoxy)benzene (mpm-5P4E),
1-(m-phenoxyphenoxy)-4-(p-phenoxyphenoxy)benzene (mpp-5P4E),
m-bis(p-phenoxyphenoxy)benzene (pmp-5P4E),
p-bis(p-phenoxyphenoxy)benzene (ppp-5P4E),
o-bis(m-phenoxyphenoxy)benzene (mom-5P4E),
m-bis(o-phenoxyphenoxy)benzene (omo-5P4E),
p-bis(o-phenoxyphenoxy)benzene (opo-5P4E),
o-bis(o-phenoxyphenoxy)benzene (ooo-5P4B) and
bis(phenoxyphenoxy)benzene isomer mixture (mix-5P4E) and
bis(phenoxyphenoxyphenyl)ether isomer mixture (mix-6P5E).

One or more of them, which are liquid in a normal state, are used.

As the particularly preferred polyphenyl ether, there can be mentioned an isomer mixture (mix-5P4E) or the like mainly comprising m-phenoxyphenoxy m-biphenyl (mm-4P2E) or m-bis (m-phenoxyphenoxy)benzene (mm-5P4E) can be mentioned.

The polyphenyl ether used as the component of the heat resistant lubricating oil composition according to the present invention is to synthesized by a production process adopted so far, for example, through Ullmann's reaction between an aromatic halogenated compound and an alkali metal salt of phenols by using a copper-based catalyst.

Organopolysiloxane

The polyorganopolysiloxane used as the component of the heat resistant lubricating oil composition according to the present invention is a polymer of an organic silicon compound having a siloxane bond as a skeleton in which hydrocarbon groups are directly bonded to the silicon atoms and represented by the following general formula [III]:

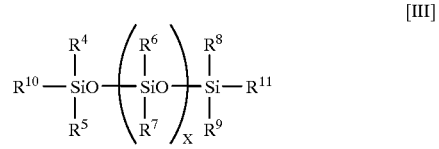

where $R^4$–$R^{11}$ which may be identical or different with each other each represent an alkyl or phenyl group. The alkyl group is, for example, a linear or branched alkyl group of 1 to 18 carbon atoms; and aryl group of 6 to 18 carbon atoms. The aryl group may be substituted with an alkyl group of 1 to 12 carbon atoms. As the alkyl group, those having 1 to 8 carbon atoms are preferred, for example, methyl group, ethyl group, propyl group, butyl group, pentyl group, hexyl group, heptyl group and octyl group, short chained groups being particularly preferred. As the aryl group, there can be mentioned, phenyl group, tolyl group, and xylyl group, phenyl group being particularly preferred. x can be selected optionally depending on the desired viscosity, which is an integer of 1 to and particularly, preferably, an integer of 1 to 5.

According to the present invention, a preferred organopolysiloxane is represented by the following general formula [IV]:

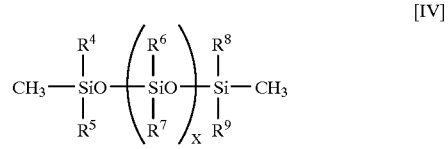

where $R^4$, $R^5$, $R^7$, $R^8$, $R^9$ which may be identical or different with each other each represent an alkyl group of 1 to 8 carbon atoms or an aryl group of 6 to 12 carbon atoms. As the alkyl group, methyl group is used most generally and other higher alkyl groups and phenyl groups are used together for the improvement of the steel-to-steel lubricity of dimethyl silicone and the improvement of the heat resistance. Specifically, there can be mentioned alkylmethyl polysiloxane and phenylmethyl polysiloxane. For example, ethylmethyl polysiloxane and octylmethyl polysiloxane are sued as the alkyl methyl polysiloxane.

In the general formula [IV], x is an integer of 1 to 10 and, preferably, an integer of 2 to 5 in view of the improvement for the viscosity and the wear resistance.

Accordingly, the phenylmethyl polysiloxane represented by the general formulas [IV] shown above is most preferred for the present invention, and it can be exemplified, more specifically, a phenylmethyl polysiloxane represented by the following structural formula (a):

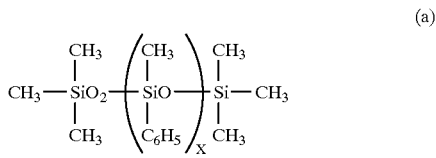

where x is an integer of 1 to 10, preferably, 1 to 5, a phenyltrimethyl trisiloxane represented by the following structural formula (b):

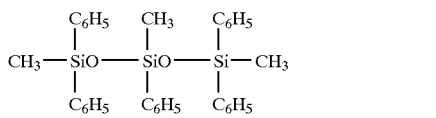

and a tetraphenyltetramethyl trisiloxane represented by the following structural formula (c):

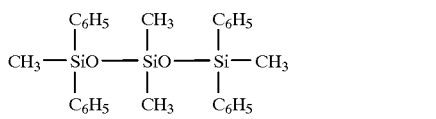

The viscosity of the lubricating base oil, while different depending on the uses, is usually 2 mm²/s–30 mm²/s and, particularly, 3 mm²/S–10 mm²/s of kinematic viscosity at 100° C. If the kinematic viscosity is less than 2 mm²/s, oil film are broken tending to cause scorching. On the other hand, if it exceeds 30 mm²/s, flowability is lowered to deteriorate the function as the lubricating oil.

As the polyol ester, commercially available Unister CA 164, an ester oil manufactured by NOF Corporation and LX 923, manufactured by Asahi Denka Kogxo K.K. can be utilized. Further, as the polyphenyl ether, commercially available m-phenoxyphenoxy m-biphenyl (m-4P2E) (S3 103, manufactured by Matsumura Petroleum Research Institute Co.) and m-bis(m-phenoxyphenoxy) benzene (m-5P4E) (S3105, manufactured by Matsumura Petroleum Research Institute Co.) can be used. Further, as the organopolysiloxane, silicone F5 and silicone F4 manufactured by Shin-Etsu Chemical Co., Ltd. can be used.

Explanation is to be made for phosphorus type anti-wear additive and sulfur type anti-wear additive and antioxidant used in the heat resistant lubricating oil composition.

Phosphorus-based anti-wear additive

As the phosphrorus-based anti-wear additive there can be mentioned phosphate ester compound represented by the general formula [V]:

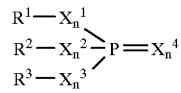

and an amine salt of such compound can be mentioned.

In the general formula [V], $R_1$ to $R_3$ which may be identical or different with each other represent each a hydrogen atom or a hydrocarbon group of 1 to 18 carbon atoms, for example, linear or branched alkyl group of 1 to 13 carbon atoms, linear or branched alkenyl group of 2 to 13 carbon atoms, cycloalkyl group of 6 to 18 carbon atoms, and aryl group of 6 to 18 carbon atoms. The aryl group may have an alkyl group of 1 to 12 carbon atoms. $X^1$–$X^4$ each represent an oxygen atom or a sulfur atom and n each is independently 0 or 1. Particularly preferred hydrocarbon group is an alkyl group and an aryl group. As the alkyl group, those having 4 to 10 carbon atoms are preferred, and there can be exemplified, for example, butyl group, pentyl group, hexyl group, heptyl group and octyl group. Further, as the aryl group, there can be mentioned, for example, phenyl group, tolyl group, xylyl group and naphtyl group.

As the compound of the general formula [V], there can be mentioned phosphate ester compounds, that is, normal phosphate, phosphite and partial esters thereof for example, triaryl phosphate, trialkyl phosphate, triaryl phosphoro thionate, trialkyl phosphonate, triaryl phosphonate, trialkyl phosphinate, triaryl phosphinate, trialkyl phosphite and triaryl phophite.

The phosphate ester having aryl group can be mentioned specifically, for example, triphenyl phosphate, tricresyl phosphate, benzyldiphenyl phosphate, ethyldiphenyl phosphate, cresyldiphenyl phosphate, dicresyl phenyl phosphate, ethylphenyldiphenyl phosphate, diethylphenylphenyl phosphate, propyiphenyl diphenyl phosphate, dipropylphenylphynyl phosphate, triethylphenylphenyl phosphate, tripropylphenyl phosphate, butylphenyldiphenyphosphate, dibutylphenylphenyl phosphate, tributylphenyl phosphate and propylphenyophenyl phosphate, and one or more of the compounds may be used. Particularly, tricresyl phosphate is preferred.

Further, acidic phosphate amine salt can also be used by which an extreme pressure property can be improved in addition to the improvement for the wear resistance. The acidic phosphate amine salt is a reaction product of an acidic phosphate and an amine compound. As the acidic phosphate, a compound represented by the general formula [V] in which one or two of $R_1$, $R_2$ and $R_3$ is a hydrogen atom can be used.

As preferred compounds of the acidic phosphate, there can be mentioned specifically, for example, dibutyl acid phosphate, dihexyl acid phosphate, di-2-ethylhexyl acid phosphate, didecyl acid phosphate, didodecyl acid phosphate (dilauryl acid phosphate), tridecyl acid phosphate, dioctadecyl acid phosphate (distearyl acid phosphate), di-9-octadecenyl acid phosphate (dioleyl acid phosphate) and a mixture thereof.

As the amine compound to be reacted with the acidic phosphate, there can be mentioned a primary or secondary amine having a hydrocarbon group of 6 to 20 carbon atoms. As the hydrocarbon group, there can be mentioned, for example, a linear or branched alkyl croup of 6 to 20 carbon atoms; a linear or branched alkenyl group of 6 to 20 carbon atoms; alkyl aryl group having an aryl group of 6 to 20 carbon atoms and a linear or branched alkyl groups and arylalkyl group. As preferred acidic phosphate amine salts, there can be mentioned, for example, a reaction product of methyl acid phosphate and a trialkyl amine of 10 to 14 carbon atoms, a reaction product of butyl acid phosphate and dodecyl phenyl amine, a reaction product of butyl acid phosphate and an alkyl aromatic amine, a reaction product of hexyl acid phosphate and ditridecyl amine, a reaction product of octyl acid phosphate and oleylamine and a reaction product of an i-$C_8$–$C_{10}$ alkyl acid phosphate and oleyl amine. Particularly, isooctyl acid phosphate amine salt [reaction product of (i-$C_8H_{17}O)_2P(OH)O$ and $C_{16}H_{33}NH_2$], 2-ethylhexyl acid phosphate amine salt [a reaction product of $((C_8H_{17}O)_2P(O)OH+C_8H_{17}OP(O)(OH)_2$ and isotridecyl amine], and di-9-octadecenyl acid phosphate amine salt (dioleyl acid phosphate amine salt) are preferred.

In addition to the acidic phosphate amine salt described above, acidic phosphite amine salt may also be used in combination.

Sulfur-based anti-wear additive

As the sulfur-based anti-wear additive used for the heat resistant lubricating oil composition according to the present invention, a sulfur compound represented by the following general formula [VI] is preferred:

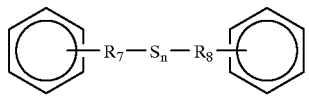

[VI]

where $R_7$ and $R_8$ represent each a hydrocarbon group of 1 to 10 carbon atoms, preferably, 1 to 5 carbon atoms. Particularly preferred hydrocarbon group is an alkylene group of 1 to 2 carbon atoms. n is an integer of 1 to 5, preferably, 1 to 3.

As the sulfur compound of the general formula [VI], a dibenzyl sulfide compound can be used specifically.

Further, as the sulfur-based anti-wear additive, sulfurfized fats and oils and other paraffinic sulfide can be used together with or independent of the sulfur compound of the general formula [VI].

Antioxidant

According to the present invention, free radical chain stopper type antioxidant, for example, diaryl amines and hindered phenols are used. As specific examples of the diaryl amines, there can be mentioned, alkylated diphenyl amines such as, p,p'-dibutyl diphenyl amine, p,p'-dipentyl diphenyl amine, p,p'-dihexyl diphenyl amine, p,p'-diheptyl diphenyl amine, p,p'-dioctyl diphenyl amine, p,p'-dinonyldiphenyl amine, monooctyl diphenyl amine, monononyl diphenyl amine, tetrabutyl diphenyl amine, tetrahexyl diphenyl amine, tetraoctyl diphenyl amine, tetranonyl diphenyl amine, and a mixed alkyl diphenyl amine having 4 to 9 carbon atoms, alkylated phenyl naphthyl amine such as phenyl-α-naphthyl amine, phenyl-β-naphthyl amine, buthylphenyl-α-naphthylamine, buthylphenyl-β-naphthyl amine, pentylphenyl-α-naphthyl amine, pentylphenyl-β-naphthyl amine, hexylphenyl-α-naphthyl amine, hexylphenyl-β-naphthyl amine, heptylphenyl-α-naphthyl amine, heptylphenyl-β-naphthyl amine, octylphenyl-α-naphthyl amine, octylphenyl-β-naphthyl amine and nonylphenyl-α-naphthyl amine, nonylphenyl-β-naphthyl amine, phenothiazine and alkylated phenothiazines.

As preferred diaryl amines, there can be mentioned, for example, p,p'-dioctyldiphenyl amine, phenyl-α-naphthyl amine and alkylphenyl-α-naphthyl amine, which may be used each alone or in combination.

As the hindered phenols, there can be mentioned, specifically, 2,6-di-t-butylphenol, 2,6-di-t-butyl-p-cresol, 2,6-di-t-butyl-4-ethylphenol, 2,4-dimethyl-6-t-butylphenol, 4,4'-methylene bis(2,6-di-t-butylphenol), 4,4'-isopropylidene bis (2,6-di-t-butylphenol), 4,4'-butylidene bis(4-methyl-6-t-butylphenol), 4,4'-thiobis (2-methyl-6-t-butylphenol) and4,4'-thio bis(3-methyl-6-t-butylphenol).

As preferred hindered phenols, there can be used 2,6-di-t-butyl-p-cresol, 4,4'-methylene bis(2,6-di-t-butylphenol) and 4,4'-methylene bis(6-t-butyl-o-cresyl) can be used.

The free radical chain stopper type antioxidant can provide a synergistic antioxidant effect by the combined use with the polyphenyl thioether in the heat resistant base oil, particularly, under a high temperature condition.

Lubricating oil Composition

The heat resistant lubricating oil composition according to the present invention comprises the lubricating base oil and the polyphenyl thioether represented by the general formula [I] described above.

As the lubricating base oil, there can be used at least one component selected from the group consisting of (a), (b) and (c): (a) an organic ester, (b) an organopolysiloxane and (c) a mixture of a polyphenyl ether and an organic ester, a mixture of a polyphenyl ether and an organopolysiloxane and a mixture of an organic ester, a polyphenyl ether and an organopolysiloxane. As the organic ester, a polyol ester is preferable.

For ensuring the function of the polyphenyl thioether as the antioxidant, the polyphenyl thioether is added to the lubricating base oil preferably from 0.05% by weight to 10% by weight, more preferably, from 0.1% by weight to 7% by weight and, particularly, from 0.2% by weight to 5% by weight based on the total weight of the lubricating oil composition. If the content of the polyphenyl thioether in the lubricating oil composition is less than 0.05% by weight, no satisfactory antioxidation effect at high temperature can be obtained. On the other hand, even if the content exceeds 10% by weight, no effective high temperature antioxidation effect can be obtained corresponding to the increased amount of addition.

The free radical chain stopper type antioxidant used in combination with the polyphenyl thioether can be added from 0.05% by weight to 3% by weight, preferably, from 0.1% by weight to 2% by weight.

Further, as the phosphorus-based anti-wear additive, the phosphate can be used from 0.5% by weight to 10% by weight and, preferably, from 1% by weight to 6% by weight, and the acidic phosphate amine salt can be used from 0.01% by weight to 1% by weight and, preferably, from 0.01% by weight to 0.5% by weight. The sulfur-based anti-wear additive can be used from 0.1% by weight to 7% by weight, preferably, from 1 % by weight to 5% by weight.

The present invention further provides a lubricating oil composition capable of maintaining the heat resistance and the oxidation resistance and excellent in the wear resistance by incorporating the polyphenyl thioether by not less than 10% by weight in the lubricating oil composition. It is extremely unique that poor anti-wear resistance of the lubricating oil composition, when the organic ester or the polyphenyl ether is used alone, can be improved by mixing the polyphenyl thioether by not less than 10% by weight.

The heat resistant lubricating oil composition according to the present invention comprises (A) from 10% by weight to 90% by weight of one of components selected from the group consisting of (a) an organic ester and/or an organopolysiloxane, or (b) an organic ester and/or an organopolysiloxane and a polyphenyl ether and (B) from 90% by weight to 10% by weight of a polyphenyl thioether. That is, there can be mentioned a mixture of an organic ester and a polyphenyl thioether, a mixture of an organopolysiloxane and a polyphenyl thioether, a mixture of an organic ester, an organopolysiloxane and a polyphenyl thioether.

Particularly, in the lubricating oil composition containing the polyol ester and the polyphenyl thioether, the mixing ratio of them is (a) from 10% by weight to 90% by weight of the organic ester, and (b) from 90% by weight to 10% by weight of the polyphenyl thioether. A particularly preferred ratio is: from 20% by weight to 80% by weight of (a) an organic ester and from 80% by weight to 20% by weight of (b) a polyphenyl thioether and, a further preferred mixing ratio is: from 40% by weight to 60% by weight of (a) an organic ester and from 60% by weight to 40% by weight of (b) a polyphenyl thioether.

The phosphorus-based anti-wear additive is an essential ingredient for the mixture of the polyphenyl ether and the polyphenyl thioether. As a mixing ratio, into a base oil consisting of (a) from 10% by weight to 90% by weight of the polyphenyl ether and (b) from 90% by weight to 10% by weight of the polyphenyl thioether, (c) a phosphorus-based anti-wear additive is added by from 0.1% by weight to 9% by weight based on the total weight of the lubricating oil composition. A preferred mixing ratio is: (a) from 15% by weight of 60% by weight of the polyphenyl ether, (b) from 85% by weight to 40% by weight of the polyphenyl thioether and (c) from 0.5% by weight to 8% by weight of the phosphorus-based anti-wear additive and, a particularly preferred mixing ratio is: (a) from 30% by weight to 55% by weight of the polyphenyl ether, (b) from 65% by weight to 45% by weight of the polyphenyl thioether and (c) from 1% by weight to 7% by weight of the phosphorus-based anti-wear additive. By mixing the polyphenyl ether and the polyphenyl thioether at the ratio described above, a lubricating base oil with a lowered flow point and having a desired viscosity can be obtained.

Further, the sulfur-based anti-wear additive is an essential ingredient for the lubricating oil composition containing the organopolysiloxane and the polyphenyl thioether. A mixing ratio is: (a) from 10% by weight to 90% by weight of the organopolysiloxane and (b) from 90% by weight to 10% by weight of the polyphenyl thioether, and a preferred ratio is: (a) from 20% by weight to 70% by weight of the organopolysiloxane and (b) from 80% by weight to 30% by weight of a polyphenyl thioether, and a particularly preferred ratio is: (a) from 40% by weight to 60% by weight of the organopolysiloxane and (b) from 60% by weight to 40% by weight of the polyphenyl thioether. The sulfur-based anti-wear additive is used within a range from 0. 1% by weight to 7% by weight, preferably, from 1% by weight to 5% by weight based on the total weight of the lubricating oil composition.

In the lubricating oil composition according to the present invention, other additives, for example, anti-wear additive, viscosity index improver, pour point depressant, corrosion inhibitor and metal deactivator can be added properly if necessary as additive ingredients.

As the anti-wear additive, there can be mentioned, for example, zinc dialkyldithiophosphate, and zinc dialkyldithiocarbamate. They are used usually at a ratio from 0.01% by weight to 5% by weight.

As the viscosity index improver, there can be used a polymethacrylate, polyisobutylene, ethylene-propylene copolymer or styrene-butadiene hydrogenated polymer-based improvers, which are used usually from 1 % by weight to 35% by weight.

As the pour point depressant, there can be used, for example, ethylene-vinyl acetate copolymer, a condensate of chlorinated paraffin and phenol, a condensate of chlorinated paraffin and naphthalene and polymethacrylate copolymer, which are used usually from 0.01% by weight to 5% by weight.

The lubricating oil composition according to the present invention can be used as a lubricating oil for various kinds of equipments such as jet engine oils, turbocharger engine oils, gas turbine oils, variable speed drive oils, diffusion pump oils, rotary pump oils, oil-impregnated plastic oils and oil-impregnated bearing oils, as well as vacuum pumpoils used under high temperature.

Production Process for Polyphenyl Thioether

As the polyphenyl thioether to be subjected to purification in the present invention, there can be mentioned those containing, for example, m-bis (phenyl-mercapto)benzene (m-3P2T), bis(m-phenylmercapto)sulfide (mm-4P3T), m-bis(m-phenylmercaptophenylmercapto)benzene(mmm-5P4T).As a typical example of them, there can be mentioned a polyphenyl thioether crude product obtained by distilling under vacuum a reaction product formed by reaction of a metal salt of a thiophenol derivative and a halogenated aromatic compound under the presence of a copper catalyst. The thus obtained polyphenyl thioether crude product is subjected to the heat treatment under the presence of an alkali metal compound and/or an alkaline earth metal compound according to the present invention. A polyphenyl thioether excellent in the heat resistance and the oxidation resistance and also excellent in the weather resistance can be obtained by applying the purifying treatment to the crude product described above, and a polyphenyl thioether of high commercial value and suitable to a wide range of uses can be provided.

The thiophenol derivative is a compound in which —SH group is bonded to an aromatic ring and there can be mentioned, specifically, thiophenol and its derivative, for example, m-phenylmercapto thiophenol and m-(m-phenylmercapto) phenylmercapto thiophenol which is properly selected and used depending on the aimed polyphenyl thioether to be obtained.

The thiophenol derivative is used as a metal salt, particularly, an alkali metal salt. As the alkali metal, any of sodium, potassium or lithium may be used, with potassium and sodium being preferred. An alkali metal salt of a thiophenol derivative can be prepared as a solution of the alkali metal salt of the thiophenol derivative by mixing the thiophenol derivative and an alkali metal hydroxide under the presence of a solvent, heating the mixture and then removing water formed. As the solvent, a polar solvent, for example, dimethylformamide, dimethylacetoamide, N-methyl-2-pyrrolidone and N-propyl-2-pyrrolidone can be used.

As the halogenated aromatic compound to be reacted with the thiophenol derivative, there can be mentioned halogenated benzene, for example, chlorobenzene and bromobenzene and, specifically, dichlorobenzene and dibromobenzene are used. In addition, other compounds may also be selected and used depending on the kind of the aimed polyphenyl thioether, for example, m-chlorophenylphenyl sulfide, p-chlorodiphenyl sulfide and m-(m-phenylmercaptophenylmercapto) phenyl chloride.

A polyphenyl thioether crude product can be obtained by reacting a thiophenol derivative and a halogenated aromatic compound, after preparing an alkali metal salt of a thiophenol derivative, in a solvent described above under the presence of a copper catalyst, or by heating a thiophenol derivative, a halogenated aromatic compound and an alkali metal hydroxide simultaneously, removing water formed, heating them and maintaining at the heated temperature with addition of a copper catalyst and collecting a fraction at 220° C.–230° C./5 Torr of the reaction product, to obtain a polyphenyl thioether crude product.

The thiophenol derivative and the halogenated aromatic compound are used at a molar ratio of 1:0.3 to 0.5, preferably, 1:0.4 to 0.5. Further, the amount of the alkali metal hydroxide used is preferably from about 0.8 to about 1.2, particularly, from about 1 to about 1.1 equimolar amount based on the thiophenol derivative. The reaction temperature is from 100° C. to 200° C., preferably, from 100° C. to 170° C. Particularly, in the reaction between the thiophenol derivative and the alkali metal hydroxide, it is, from 100° C. to 150° C., and preferably, from 120° C. to 150° C. In the reaction between the alkali metal salt of the thiophenol derivative and the halogenated aromatic compound, it is from 160° C. to 210° C., preferably, from 180° C. to 210° C. The reaction time is optionally selected but it is determined based on a GPC measurement of the reaction product, and it is usually from about 6 to 10 hours. As the reaction system either a batchwise or a continuous production process can be adopted properly.

As the copper catalyst, any of catalysts may be used so long as it contains at least cuprous chloride, cupric chloride, cuprous oxide, cupric oxide or copper powder, with the cuprous chloride-containing catalyst being preferred. The amount of the copper may be a catalytically effective amount and, usually, it is added by not less than 1 mol %, preferably, from 5 mol % to 25 mol % based on 1 mol of the thiophenol derivative.

The thiophenol derivative and the halogenated aromatic compound are reacted under the reaction conditions described above, subjected to distillation under a reduced pressure as it is or after filtration, to obtain a polyphenyl thioether crude product fraction. For example, by the reaction between a potassium salt of thiophenol and m-dichlorobenzene, a m-bis(phenylmercapto) benzene crude product can be obtained as a fraction at 220° C.–230° C./5 Torr.

Then, a method of the heat treatment according to the present invention is to be explained.

The polyphenyl thioether prepared as described above is subjected to a heat treatment under the presence of an alkali metal compound and/or an alkaline earth metal compound. As the alkali metal compound, sodium, potassium or lithium hydroxide is preferred. Further, as the alkaline earth metal compound, magnesium hydroxide or calcium hydroxide can be used, with alkali metal hydroxide, particularly, sodium hydroxide and potassium hydroxide being preferred. The amount of use can be determined properly depending, for example, on the quality of the polyphenyl thioether to be treated and it can be used usually of more than about 50 g based on 1 kg of the starting polyphenyl thioether and is preferably selected by an appropriate amount in view of economical points or the like. Specifically, the heat treatment is applied by adding an alkali metal hydroxide and/or an alkaline earth metal hydroxide in the reaction system.

The method for the heat treatment can be optionally selected and adopted and, for example, an alkali metal hydroxide may be added to the starting polyphenyl thioether and heating operation can be applied in the mixed state. Further, the starting polyphenyl thioether may be brought into contact with an alkali metal hydroxide by passing through a layer filled with the hydroxide, but a method of mixing the alkali metal hydroxide in the starting polyphenyl thioether and subjecting them to the heat treatment is preferred.

According to the present invention, the heat treatment is carried out under the condition of a reduced pressure. That is, a condition of lower than about 100 mmHg, preferably, from about 1 mmHg to about 50 mmHg and, more preferably, from about 1 mmHg to about 10 mmHg is adopted. The reduced pressure condition of about 100 mmHg is used because of suppression for the effect of oxidation due to oxygen. Under a normal pressure, the heat treatment has to be applied under an elevated temperature and, as a result, this brings about a problem of quality deterioration of the polyphenyl thioether compound.

The temperature for the heat treatment is lower than the refluxing temperature of the starting polyphenyl thioether and the temperature can be adapted within a range preferably from about 200° C. to about 300° C. and, particularly preferably, from 200° C. to 250° C. If the temperature for the heat treatment is excessively high, a problem of carbonization occurs.

There is no particular restriction on the treating time and it may be usually about more than 1 hour and, preferably, from about 3 hours to about 6 hours.

Accordingly, as can be seen from the foregoing explanation, in a preferred embodiment for the heat treatment, an alkali metal hydroxide such as potassium hydroxide is mixed to the polyphenyl thioethers, they are subjected to distillation under reduced pressure and purified distillation products can be collected as purified fraction of polyphenyl thioether.

EXAMPLE

The present invention is to be explained more specifically with reference to Examples and Comparative Examples.

Performances such as heat resistance, oxidation resistance and wear resistance of each of lubricating oil compositions obtained in the Examples were evaluated by a corrosion-oxidation stability test and a wear test by a 4-ball tester shown later.

Corrosion-Oxidation Stability Test (COS Test)

This test method is determined according to USAF MIL-L-23699 Standards. 100 ml of a sample oil was subjected to an oxidation treatment by using Ag, Al, Fe and Ti as an oxidation catalyst at a temperature of 218° C. or 230° C. for 72 hours while blowing air at a rate of 5 liter/hour. Then, weight change of metal pieces, viscosity change, change of total acid number before and after the oxidation treatment and the amount of sludges formed after the oxidation treatment were measured as the results of evaluation for the heat resistance and the oxidation resistance.

Among the test items described above, the weight change of the metal pieces is evaluated as satisfactory when the change is less than ±0.2 mg/cm$^2$ for the weight change/surface area of the metal piece. The viscosity change is the kinematic viscosity variation coefficient (%) at 40° C., the change of the total acid number is a difference of the total acid number (mg KOH/g), and the amount of the sludge formed is the weight of the remaining specimen oil after the oxidation treatment and filtration through a filter of 10 μm pore size manufactured by Milipore Co. based on the residue per 100 ml of the specimen oil (mg/100 ml).

Wear Test

In a wear test by using Shell 4-ball tester the wear track diameter of a test ball is measured in accordance with ASTM D4172. The following test conditions are employed and test balls of the following three kinds of materials are used as rotational balls and fixed stationary balls as shown in each of examples. Wear track diameters (mm) of three stationary balls after 30 min's operation were measured to determine a mean value of them.

Test Conditions:

Temperature (°C.): 80

Load (kg): 30

Number of rotation (rpm): 1,200

Test ball: SUJ-2 (high carbon chromium steel)
M-50 (heat resisting steel)
$Si_3N_4$ (silicon nitride ceramics)

The lubricating base oil used in Examples and Comparative Examples are as follows.

Note 1) Pentaerythritol ester A: Ester of pentaerythritol and n-pentanoic acid (Unistar CA164, ester oil manufactured by NOF Corporation.)

Note 2) Pentaerythritol ester B: Ester of pentaerythritol and n-hexanoic acid (LX923, ester oil manufactured by Asahi Denka Kogyo K.K.)

Note 3) Pentaerythritol ester C: Ester of pentaerythritol and mixed $C_5$–$C_9$ aliphatic acid (P-51, Ester oil manufactured by Mobile Oil Corporation.)

Note 4) Pentaphenyl trimethyl trisiloxane: (Silicone F5 manufactured by Shin-Etsu Chemical Co., Ltd.)

Note 5) Acidic phosphate amine salt: Compound of butyl acid phosphate and p-dodecyl aniline Note 6) Dipentaerythritol ester: Ester of dipentaerythritol and a mixture of iso-pentanoic acid and n-hexanoic acid (LX-810, Ester oil manufactured by Asahi Denka Kogyo K.K.)

Note 7) Tripentaerythritol ester: Ester of tripentaerythritol and a mixture of iso-pentanoic acid and n-hexanoic acid (LX-889, Ester oil manufactured by Asahi Denka Kogyo K.K.)

Note 8) Ditrimethylolpropane ester: Ester of ditrimethylolpropane and n-heptanoic acid (LX-1342, Ester oil manufactured by Asahi Denka Kogyo K.K.)

Note 9) Bis(m-phenoxyphenyl) ether (mm-4P3E): Trial product

Note 10) Dibenzyl disulfide: Dailube S-700, manufactured by Dainippon Ink and Chemicals Inc.

Note 11) Sulfurized fat and oil: Dailube S-320, manufactured by Dainippon Ink and Chemicals Inc.

Example X-1

Bis(m-phenylmercaptophenyl)sulfide (mm-4P3T) was added to pentaerysthritol ester A by 1% by weight based on the total weight of the lubricating oil composition, to obtain a lubricating oil composition having kinematic viscosity at 40° C. and 100° C. of 17.4 cSt and 3.8 cSt, respectively and a viscosity index of 105. Further, octylphenyl-α-naphthyl amine and p,p'-di-octyldiphenyl amine and tricresyl phosphate were added each as shown in Table 1.

Then, the lubricating oil composition was subjected to performance evaluation as described above. The results are shown in Table 1.

Example X-2

A lubricating oil composition was prepared quite in the same procedures as those in Example X-1 except for using m-bis(m-phenylmercaptophenylmercapto) benzene (mmm-5P4T) instead of bis(m-phenylmercaptophenyl)sulfide (mm-4P3T). The results of the performance evaluation are shown in Table 1.

Examples X-3~X-4

Lubricating oil compositions having compositions shown in Table 1 were prepared by using pentaerythritol ester C as a base oil, and using m-bis(m-phenylmercapto)benzene (m-3P2T) by 1% by weight (Example X-3) and 4% by weight (Example X-4). Results of the performance evaluation are shown in Table 1.

Example X-5

A lubricating oil composition having a composition shown in Table 1 was prepared by using pentaerythritol C as a base oil, and using 4% of by weight $C_{18}$ alkyl diphenyl sulfide (R-2P1T). Results of the performance evaluation are shown in Table 1.

Example X-6 m-bis(m-phenylmercapto)benzene (m-3P2T) was added by 4% by weight to a mixed base oil of pentaerythritol ester C and m-phenoxyphenoxybiphenyl (m-4P2E) to prepare a lubricating oil composition shown in Table 1. Results of the performance evaluation for the lubricating oil composition are shown in Table 1.

Example X-7

$C_{12}$ alkyl m-bis(m-phenylmercapto)benzene was added by 4% by weight to a mixed base oil of pentaerythritol ester B and pentaphenyltrimehyl trisiloxane to prepare a lubricating oil composition shown in Table 1. Results of the performance evaluation for the lubricating oil composition are shown in Table 1.

Example X-8 m-bis(m-phenylmercapto)benzene (m-3P2T) was added by 10% by weight to pentaerythritol ester C to prepare a lubricating oil composition shown in Table 1. Results of the performance evaluation are shown in Table 1.

Examples X-9~Example X-15

The lubricating base oils and additives shown in Table 1 were mixed each at a ratio shown in the Table 1. Results of the performance evaluation for the lubricating oil compositions obtained are shown in the table.

Comparative Examples X-1~X-5

Only octylphenyl-α-naphthyl amine, p,p'-dioctyldiphenyl amine and tricresyl phosphate were added each at a ratio shown in Table 2, without adding polyphenyl thioether, to pentaerythritol ester A(Comparative Example X-1), pentaerythritol ester B(Comparative Example X-2), a mixture of pentaerythritol ester B and pentaphenyltrimethyl trisiloxane (Comparative Example X-3), pentaerythritol ester C(Comparative Example X-4) and a mixture of pentaerythritol ester C and m-phenoxyphenoxy-m-biphenyl (m-4P2E) (Comparative Example X-5). Results of the performance evaluation for the resultant lubricating oil compositions are shown in the table.

Since Examples X-1~X-15 showed less total acid number change and gave considerably smaller amount of sludges as compared with any of the Comparative Examples, a combined effect of the specified heat resistant base oil such as the polyol ester and the polyphenyl thioether according to the present invention can be provided to actually attain heat resistant lubricating oils having remarkably excellent heat resistance and oxidation resistance.

Examples X-16~X-19, Comparative Example X-6

Lubricating oil compositions comprising a mixture of 40% by weight of pentaerythritol ester A and 60% by weight of m-phenoxyphenoxy-m-biphenyl (m-4P2E) as a base oil and containing m-bis(phenylmercapto)benzene (m-3P2T), tricresyl phosphate, octylphenyl-α-naphthyl amine, p,p'-dioctyldiphenyl amine and an acidic phosphate amine salt (reaction product of butyl acid phosphate and p-dodecyl aniline) each at a ratio shown in Table 3 were prepared. When each of the lubricating oil compositions was subjected to the performance evaluation, results as shown in Table 3 were obtained.

TABLE 1

| | EXAMPLES | | | | | | | | | | | | | | |
|---|---|---|---|---|---|---|---|---|---|---|---|---|---|---|---|
| | X-1 | X-2 | X-3 | X-4 | X-5 | X-6 | X-7 | X-8 | X-9 | X-10 | X-11 | X-12 | X-13 | X-14 | X-15 |
| Base oil (wt. %) | | | | | | | | | | | | | | | |
| Pentaerythritol ester A$^{Note\ 1)}$ (C$_5$ acid) | 92 | 92 | | | | | | | | | | | | | |
| Pentaerythritol ester B$^{Note\ 2)}$ (C$_6$ acid) | | | | | | | 56 | | | | | | | | |
| Pentaerythritol ester C$^{Note\ 3)}$ (C$_5$~C$_9$ acid) | | | 92 | 89 | 89 | 44.5 | | 83 | 55 | 55 | 92 | 92 | 92 | 92 | 92 |
| m-Phenoxyphenoxy m-biphenyl (m-4P2E) | | | | | | 44.5 | | | 37 | | | | | | |
| Pentaphenyl trimethyl trisiloxane$^{Note\ 4)}$ | | | | | | | 37 | | | 37 | | | | | |
| Additive (wt. %) | | | | | | | | | | | | | | | |
| m-Bis(phenylmercapto)benzene (m-3P2T) | | | 1 | 4 | | 4 | | 10 | 1 | 1 | | | | | |
| C$_{18}$ alkyldiphenyl sulfide (R-2P1T) | | | | | 4 | | | | | | 1 | | | | |
| C$_{12}$ alkyl m-bis(phenylmercapto)benzene (R-m-3P2T) | | | | | | | | 4 | | | | 1 | | | |
| Bis(m-phenylmercaptophenyl)sulfide (mm-4P3T) | 1 | | | | | | | | | | | | | 1 | |
| m-bis(m-phenylmercaptophenylmercapto)-benzene (mmm5P4T) | | 1 | | | | | | | | | | | | | 1 |
| Diphenyl sulfide (2P1T) | | | | | | | | | | | | | 1 | | |
| Octylphenyl-α-naphthylamine | 1.5 | 1.5 | 1.5 | 1.5 | 1.5 | 1.5 | 0.5 | 1.5 | 1.5 | 1.5 | 1.5 | 1.5 | 1.5 | 1.5 | 1.5 |
| p,p'-dioctyldiphenylamine | 1.5 | 1.5 | 1.5 | 1.5 | 1.5 | 1.5 | 0.5 | 1.5 | 1.5 | 1.5 | 1.5 | 1.5 | 1.5 | 1.5 | 1.5 |
| Tricresyl phosphate | 4 | 4 | 4 | 4 | 4 | 4 | 2 | 4 | 4 | 4 | 4 | 4 | 4 | 4 | 4 |
| Vis (cSt) | | | | | | | | | | | | | | | |
| @ 40° C. | 17.4 | 17.4 | 25.6 | 25.4 | 25.9 | 38.9 | 24.8 | 23.8 | 43.6 | 34.7 | 24.8 | 24.9 | 25.2 | 24.8 | 24.8 |
| @ 100° C. | 3.8 | 3.8 | 5.0 | 4.1 | 5.0 | 5.5 | 4.7 | 4.7 | 5.7 | 5.7 | 4.9 | 4.9 | 4.9 | 4.9 | 4.9 |
| Viscosity index (VI) | 105 | 105 | 121 | 115 | 121 | 62 | 109 | 116 | 52 | 103 | 126 | 124 | 122 | 126 | 126 |
| COS Test 218° C. | | | | | | | | | | | | | | | |
| Weight change of metal peice | | | | | | | Passed | | | | | | | | |
| Change of TAN (mg KOH/g) | 2.8 | 2.7 | 4.3 | 2.5 | 4.4 | 2.3 | 4.9 | 1.3 | 2.8 | 3.2 | 5.2 | 4.8 | 4.5 | 4.2 | 4.1 |
| Amount of sludge (g) | 0.2 | 0.2 | 5.2 | 2.2 | 2.1 | 1.3 | 2.3 | 2.9 | 1.5 | 1.3 | 1.7 | 2.5 | 4.4 | 2.3 | 2.5 |

$^{Note)}$The amount of each gradients is shown as % by weight based on a lubricating oil composition.

TABLE 2

| | COMPARATIVE EXAMPLES | | | | |
|---|---|---|---|---|---|
| | X-1 | X-2 | X-3 | X-4 | X-5 |
| Base oil (wt. %) | | | | | |
| Pentaerythritol ester A$^{Note\ 1)}$ (C$_5$ acid) | 93 | | | | |
| Pentaerythritol ester B$^{Note\ 2)}$ (C$_6$ acid) | | 93 | 58 | | |
| Pentaerythritol ester C$^{Note\ 3)}$ (C$_5$~C$_9$ acid) | | | | 93 | 46.5 |
| m-Phenoxyphenoxy m-biphenyl (m-4P2E) | | | | | 46.5 |
| Pentaphenyl trimethyl trisiloxane$^{Note\ 4)}$ | | | 39 | | |
| Additive (wt. %) | | | | | |
| m-Bis(phenylmercapto)benzene (m-3P2T) | | | | | |
| C$_{18}$ alkyldiphenyl sulfide (R-2P1T) | | | | | |
| C$_{12}$ alkyl m-bis(phenylmercapto)benzene (R-m-3P2T) | | | | | |
| Bis(m-phenylmercaptophenyl)sulfide (mm-4P3T) | | | | | |
| m-bis(m-phenylmercaptophenylmercapto)-benzene (mmm5P4T) | | | | | |
| Diphenyl sulfide (2P1T) | | | | | |
| Octylphenyl-α-naphthylamine | 1.5 | 1.5 | 0.5 | 1.5 | 1.5 |
| p,p'-dioctyldiphenylamine | 1.5 | 1.5 | 0.5 | 1.5 | 1.5 |
| Tricresyl phosphate | 4 | 4 | 2 | 4 | 4 |
| Vis (cSt) | | | | | |
| @ 40° C. | 17.4 | 20.4 | 24.8 | 26.0 | 41.4 |
| @ 100° C. | 3.8 | 4.3 | 4.7 | 5.0 | 5.6 |
| Viscosity index (VI) | 105 | 117 | 109 | 120 | 60 |
| COS Test 218° C. | | | | | |
| Weight change of metal peice | | | Passed | | |
| Change of TAN (mg KOH/g) | 5.3 | 5.3 | 10.2 | 7.3 | 6.2 |
| Amount of sludge (g) | 0.3 | 1.2 | 7.2 | 11.0 | 2.6 |

$^{Note)}$The amount of each gradients is shown as % by weight based on a lubricating oil composition.

TABLE 3

| | EXAMPLES | | | | COMPARATIVE EXAMPLES |
|---|---|---|---|---|---|
| | X-16 | X-17 | X-18 | X-19 | X-6 |
| Base oil | | | | | |
| Pentaerythritol ester A 40 wt. % | 95.7 | 95.6 | 95.4 | 95.2 | 99.7 |
| m-Penoxyphenoxy m-bipheny (m-4P2E) 60 wt. %[Note 1] | | | | | |
| Additive | | | | | |
| m-Bis(phenylmercapto)benzene (m-3P2T) | 2 | 2 | 2 | 2 | — |
| Acidic phosphate amine salt[Note 6] | — | 0.1 | 0.3 | 0.5 | — |
| Tricresyl phosphate | 2 | 2 | 2 | 2 | — |
| Octylphenyl-α-naphtylamine | 0.12 | 0.12 | | | |
| p,p'-dioctyldiphenylamine | 0.14 | 0.14 | | | |
| COS test 230° C. x 72 hrs | | | | | |
| Weight change of metal piece | Passed | Passed | Passed | Passed | Passed |
| Viscosity change (%) | 3.1 | 22.1 | 20.5 | 24.8 | 48.5 |
| Change of TAN (mg KOH/g) | 0.3 | 1.8 | 1.7 | 1.9 | 4.8 |
| Amount of sludge (mg/100 ml) | 0.1 | 0.1 | 0.6 | 0.8 | 2.5 |
| Four-ball wear test | | | | | |
| Wear track (mm) | | | | | |
| M-50/M-50 | 0.53 | 0.43 | 0.45 | 0.44 | 0.65 |
| SUJ-2/SUJ-2 | 0.54 | 0.45 | 0.47 | 0.46 | 0.66 |
| Extreme Pressure test | | | | | |
| (Shell EP test) | | | | | |
| Max. non-seizure load (kgf) | 40 | 50 | 63 | 63 | 40 |

It can be seen from the above results that when the acidic phosphate amine was used in addition to m-bis (phenylmercapto)benzene, the wear resistance and the extreme pressure property represented by the wear track diameter and the maximum non-seizure load can be further improved without deteriorating the heat resistance and the oxidation resistance.

Examples Y-1~Y-5

Dipentaerythritol ester, tripentaerythritol ester, ditrimethylolpropane ester and m-bis(phenylmercapto)benzene (m-3P2T) were mixed each at a ratio shown in Table 4 to prepare lubricating oil compositions shown in the table. Results for the performance evaluation are shown respectively in Table 4.

Comparative Examples Y-1~Y-4

As shown in Table 4, dipentaerythritol ester, tripentaerythritol ester, ditrimethylol propane ester and m-bis (phenylmercapto)benzene (m-3P2T) were used each alone, to prepare lubricating oil compositions as shown in Table 4. Results for the performance evaluation are shown in the table.

In Table 4, the content of the base oil ingredients is represented by % by weight on the weight basis of the base oil, and the content of the additives is represented by % by weight based on the total weight of the lubricating oil composition.

Further, in the 4-ball test, stationary ball is shown on the right and the rotary ball is shown on the left of the material indication.

Example Y-6

A lubricating base oil containing 66% by weight of m-phenoxyphenoxy-m-biphenyl (mm-4P2E) and 34% by weight of m-bis(phenylmercapto)benzene (m-3P2T) was prepared, to which tricresyl phosphate was added by 4% by weight based on the total weight of the composition, to obtain a lubricating oil composition shown in Table 5.

Example Y-7

Tricresyl phosphate was added by 4% by weight to a mixture comprising 70% by weight of bis(m-phenoxyphenyl) ether (mm-4P3E) and 30% by weight of m-bis(phenylmercapto benzene (m-3P2T) to obtain a lubricating oil composition shown in Table 5.

Comparative Examples Y-5~Y-9

Lubricating base oils and additives shown in Table 5 were mixed each at a ratio shown in the table, to obtain lubricating oil compositions.

Example Y-8

Dibenzyl sulfide was added by 5% by weight to a lubricating base oil containing 60% by weight of pentaphenyltrimethyl trisiloxane and 40% by weight of m-bis (phenylmercapto)benzene (m-3P2T), to prepare a lubricating oil composition.

Example Y-9

A lubricating oil composition was prepared quite in the same procedures as those in Example Y-8 except for adding 5% by weight of sulfurized fat and oil instead of dibenzyl disulfide, to prepare a lubricating oil composition.

Comparative Examples Y-10~Y-13

Lubricating base oils and additives shown in Table 6 were mixed each at a ratio shown in the table, to obtain lubricating oil compositions.

TABLE 4

| | EXAMPLES | | | | | COMPARATIVE EXAMPLES | | | |
|---|---|---|---|---|---|---|---|---|---|
| | Y-1 | Y-2 | Y-3 | Y-4 | Y-5 | Y-1 | Y-2 | Y-3 | Y-4 |
| Base oil (wt. %) | | | | | | | | | |
| Tripenterythritol ester[Note 7] | | 50 | | | | | 100 | | |
| Ditrimethylolpropane ester[Note 8] | | | | | 50 | | | 100 | |
| Dipentaerythritol ester[Note 6] | 50 | | 80 | 20 | | 100 | | | |
| m-bis(phenylmercapto)benzene (m-3P2T) | 50 | 50 | 20 | 80 | 50 | — | — | — | 100 |
| Addivite (wt. %) | | | | | | | | | |
| Tricresyl phosphate | 4 | 4 | 4 | 4 | 4 | 4 | 4 | 4 | 4 |
| Kinematic Vis (cSt) | | | | | | | | | |
| 40° C. | 25.0 | 36.0 | 46.1 | 15.0 | 19.0 | 72.1 | 202.0 | 34.7 | 11.0 |
| 100° C. | 4.8 | 6.2 | 7.3 | 3.4 | 4.1 | 10.0 | 20.2 | 6.5 | 2.8 |
| Viscosity Index | 113 | 121 | 121 | 98 | 117 | 122 | 112 | 143 | 79 |
| COS test 230° C × 72 H | | | | | | | | | |
| Viscosty Change (%) | 2.0 | 1.8 | 23.8 | 1.5 | 2.5 | 298 | 225 | 320 | 0.3 |
| Change of TAN (mgKOH/g) | 0.9 | 0.8 | 1.2 | 0.3 | 1.3 | 29.5 | 21 | 35 | 0 |
| Weight change of metal piece | Passed | Passed | Passed | Passed | Passed | Unpassed | | | Passed |
| Amount of sludge (mg/100 ml) | 3.2 | 2.5 | 4.8 | 2.0 | 3.3 | 98 | 58 | 110 | 0.5 |
| Four ball wear test | | | | | | | | | |
| Wear track (mm) | | | | | | | | | |
| SUJ-2/SUJ-2 | 0.41 | 0.40 | 0.39 | 0.46 | 0.42 | 0.54 | 0.52 | 0.57 | 1.10 |
| M-50/M-50 | 0.47 | 0.45 | 0.42 | 0.53 | 0.48 | 0.57 | 0.55 | 0.60 | 1.20 |
| $Si_3N_4$/M-50 | 0.51 | 0.50 | 0.51 | 0.55 | 0.53 | 0.50 | 0.45 | 0.55 | 0.66 |
| $Si_3N_4$/$Si_3N_4$ | 0.65 | 0.63 | 0.68 | 0.67 | 0.63 | 1.03 | 0.98 | 1.05 | 0.64 |

\* The content of base oil components is expressed as % by weight based on the weight of the base oil. The content of additives is expressed as % by weight based on the total weight of lubricating oil composition.
\* In the four ball wear test, the right hand side of the material indication shows a stationl ball, on the other hand the left hand side shows a rotaing ball.

TABLE 5

| | EXAMPLES | | COMPARATIVE EXAMPLES | | | | |
|---|---|---|---|---|---|---|---|
| | Y-6 | 7-7 | Y-5 | Y-6 | Y-7 | Y-8 | Y-9 |
| Base oil (wt. %) | | | | | | | |
| m-Phenoxyphenoxy m-biphenyl (mm-4P2E) | 66 | — | 66 | — | 100 | — | — |
| Bis(m-phenoxyphenyl)ether (mm-4P3E) | — | 70 | — | 70 | — | — | 100 |
| m-bis(phenylmercapto)benzene (m-3P2T) | 34 | 30 | 34 | 30 | — | 100 | — |
| Additive (wt. %) | | | | | | | |
| Tricresyl phosphate | 4 | 4 | — | — | 4 | 4 | 4 |
| Dibenzyl disulfide | | | | | | | |
| Kinematic Vis (cSt) | | | | | | | |
| 40° C. | 43.8 | 31.3 | 44.2 | 31.6 | 121.3 | 11 | 548 |
| 100° C. | 5.0 | 4.6 | 5.1 | 4.6 | 7.3 | 2.8 | 5.9 |
| Viscosity index | −30 | 25 | −17 | 22 | −107 | 79 | 7 |
| Pour point (° C.) | −15.0 | −27.5 | −12.5 | −25.0 | 2.5 | −40 | −12.5 |
| COS test 230° C × 72 H | | | | | | | |
| Viscosity change (%) | 2.5 | 2.3 | 2.6 | 2.5 | 6.2 | 3.4 | 5.8 |
| Change of TAN (mg KOH/g) | 0.1 | 0.1 | 0 | 0 | 0.1 | 0 | 0.1 |
| Weight change of metal piece | Passed | Passed | Passed | Passed | Passed | Passed | Passed |
| Amount of sludge (mg/100 ml) | 2.9 | 2.1 | 3.2 | 2.3 | 2.8 | 1.1 | 2.5 |
| Four ball wear test | | | | | | | |
| Wear track (mm) | | | | | | | |
| SUJ-2/SUJ-2 | 0.69 | 0.68 | 1.42 | 1.38 | 2.02 | 1.15 | 2.56 |
| M-50/M-50 | 0.63 | 0.62 | 1.39 | 1.35 | 3.55 | 1.20 | 3.14 |
| $Si_3N_4$/M-50 | 0.52 | 0.55 | 0.56 | 0.59 | 0.53 | 0.66 | 0.55 |
| $Si_3N_4$/$Si_3N_4$ | 0.53 | 0.54 | 0.57 | 0.75 | 0.64 | 0.78 | |

\* The content of base oil components is expressed as % by weight based on the weight of the base oil. The content of additives is expressed as % by weight based on the total weight of lubricating oil composition.
\* In the four ball wear test, the right hand side of the material indication shows a stationl ball, on the other hand the left hand side shows a rotaing ball.

TABLE 6

|  | EXAMPLES | | COMPARATIVE EXAMPLES | | | |
|---|---|---|---|---|---|---|
|  | Y-8 | Y-9 | Y-10 | Y-11 | Y-12 | Y-13 |
| Base oil (wt. %) | | | | | | |
| Pentaphenyl trimethyl trisiloxane[Note 4] | 60 | 60 | 100 | — | 60 | 60 |
| m-Bis(phenylmercapto)benzene | 40 | 40 | — | 100 | 40 | 40 |
| Additive (wt. %) | | | | | | |
| Dibenzyl disulfide[Note 10] | 5 | — | — | — | — | — |
| Sulfurized fats and oils | — | 5 | — | '3 | — | — |
| Tricresyl phosphate | — | — | — | 4 | — | 4 |
| Kinematic Vis. (cSt) | | | | | | |
| 40° C. | 27.7 | 27.7 | 62.7 | 11.0 | 28.0 | 27.9 |
| 100° C. | 4.7 | 4.7 | 7.9 | 2.8 | 4.8 | 4.7 |
| Viscosity index | 78 | 78 | 89 | 79 | 84 | 76 |
| COS test 230° C × 72 H | | | | | | |
| Viscosity change (%) | 7.0 | 6.8 | 0.2 | 0.3 | 8.0 | 10.0 |
| Change of TAN (mg KOH/g) | 0.0 | 0.0 | 0.0 | 0.0 | 0.0 | 0.2 |
| Weight change of metal piece | Passed | Passed | Passed | Passed | Passed | Passed |
| Amount of sludge (mg/100 ml) | 0.0 | 0.0 | 1.8 | 0.5 | 0.0 | 1.0 |
| Four ball wear test | | | | | | |
| Wear track (mm) | | | | | | |
| SUJ-2/SUJ-2 | 0.50 | 0.48 | 4.0 | 1.10 | 2.30 | 2.20 |
| M-50/M-50 | 0.57 | 0.52 | 4.0 | 1.20 | 2.38 | 2.26 |
| Si$_3$N$_4$/M-50 | 0.46 | 0.42 | 0.73 | 0.66 | 0.62 | 0.60 |
| Si$_3$N$_4$/Si$_3$N$_4$ | 0.44 | 0.40 | 0.45 | 0.64 | 0.55 | 0.52 |

* The content of pentaphenyl trimethyl trisiloxane and m-bis(phenylmercapto)benzene, as a base oil, is expressed as % by weight based on the weight of the base oil. The content of each additives is % by weight based on the total weight of the lubricating oil composition containing the base oil and the additive.

In view of the evaluation results described above, it is unique that the wear resistance of polyol ester, polyphenyl ether, organopolysiloxane and polyphenyl thioether can be improved remarkably by mixing them although the wear resistance is poor when each of them is used alone even if the anti-wear additive is added. Further, it has been apparent for the anti-wear additive that the phosphorus-based anti-wear additive is effective to a mixed oil of polyester/polyphenyl ether/polyphenyl thioether, whereas it is not effective to a mixed oil of organopolysiloxane and polyphenyl thioether, and the sulfur-based anti-wear additive is effective selectively.

Example Z-1

To a four-necked flask of 2 liter inner volume equipped with a water measuring tube, a cooling tube and a stirrer, 500 ml of N-methyl-2-pyrrolidone was charged, 770 g (7 mol) of thiophenol and 392.7 g (7 mol) of potassium hydroxide were added and, further, 511 g (3.5 mol) of m-dichlorobenzene was added and stirred. They were heated in an oil bath till 170° C. and the contents were separated by the water measuring tube into two layers, that is, an upper layer consisting of water and a lower layer consisting of N-methyl-2-pyrrolidone and m-dichlorobenzene, from which 126 g of water was removed.

After cooling the contents to a room temperature, 70 g of cuprous chloride was added. Then, they were heated at 210° C., reacted at that temperature for 10 hours under stirring and filtered after the completion of the reaction. The liquid filtrate was subjected to atmospheric distillation at 180° C. to 210° C., and unreacted thiophenol, m-dichlorobenzene and N-methyl-2-pyrrolidone were removed at 180° C.–210° C.

Then, from the distillation residues removed with the unreaction products, 617 g of a fraction 220° C.–230° C./5 Torr was obtained as m-bis(phenylmercapto) benzene (m-3P2T) by vacuum distillation. The yield of m-bis (phenylmercapto) benzene (m-3P2T) relative to m-dichlorobenzene was 60%.

It was confirmed by gel permeation chromatograph (GPC) that the fraction was a reaction product of a single composition and it was confirmed to be m-bis(phenylmercapto) benzene (m-3P2T) by mass spectrometric analysis (FD method: using DX-303 manufactured by Nippon Denshi Co.). In the gel permeation chromatograph, LC-6A manufactured by Shimazu Seisakusho Co. assembled by connecting each of columns of 38 cm length and filled with SHOWDEX G-4000HXL G-2500HXL and G-2000HXL manufactured by Showa Denko K.K. respectively was used as an analysis column.

600 g of m-bis(phenylmercapto)benzene (n-3P2T) fraction obtained as described above was charged into a four-necked flask of 2 liter inner volume equipped with a stirrer, a thermometer and a reflux condenser tube, to which 30 g of potassium hydroxide was added and subjected to a heat treatment for about three hours under reflux while reducing pressure (to 100 mmHg) by a vacuum pump. After the heat treatment, a Widmer pipe was attached and fractional distillation was conducted under a reduced pressure, to obtain 540 g of the polyphenyl thioether containing m-bis (phenylmercapto)benzene. This is referred to as a trial product A. The results of the performance evaluation are shown in Table 7.

Example Z-2

600 g of the polyphenyl thioether fraction was treated in the same procedures as those in Example Z-1 except for using 18 g of sodium hydroxide instead of potassium hydroxide, to obtain 530 g of polyphenyl thioether containing m-bis(phenylmercapto)benzene. This was referred to as trial product B. Results of the performance evaluation are shown in Table 7.

Example Z-3

436 g of m-phenylmercapto thiophenol and 78 g of potassium hydroxide were dissolved in 500 ml of N-methyl-2-pyrrolidone, then 376 g of m-chlorophenyl phenylsulfide was added and the resultant mixture was heated to 170° C. After removing the water content, 20 g of cuprous chloride was added and heated to 210° C. and maintained at that temperature for 10 hours while stirring. After the reaction was over, the product was treated by the method as in Example Z-1 and bis(m-phenylmercaptophenyl)sulfide was obtained as a fraction at 255° C.–265° C./5 Torr by vacuum distillation.

33 g of potassium hydroxide was added to 650 g, of thus obtained bis(m-phenylmercaptophenyl)sulfide and subjected to a heat treatment for about 3 hours under reflux at 290° C.–300° C. by reducing the pressure (to 100 mmHg) by a vacuum pump. Then, the reaction products were rectified by the same operation as in Example Z-1, to obtain bis(m-phenylmercaptophenyl)sulfide. This was referred to as trial product C. Results of the performance evaluation are shown in Table 7.

relative to m-dichlorobenzene was 60%. The product (comparative oil A) was subjected to the above-mentioned performance evaluation without heat treatment under the presence of potassium hydroxide.

Comparative Example Z-2

436 g of m-phenylmercapto thiophenol and 78 g of potassium hydroxide were dissolved in 500 ml of N-methyl-2-pyrrolidone, then 376 g of m-chlorophenyl phenylsulfide was added and the resultant mixture was heated to 170° C. After removing the water content, 20 g of cuprous chloride was added and heated to 210° C. and maintained at that temperature for 10 hours while stirring. After the reaction was over, the reaction product was treated by the same procedures as in Example Z-1 and bis(m-phenylmercaptophenyl)sulfide was obtained as a fraction at 255° C.–265° C./5 Torr by vacuum distillation. The product was referred as a comparative oil B and subjected to performance evaluation described above.

From the result of evaluation described above, it was found that the polyphenyl thioether products after the purifying treatment according to the present invention did not discolor even after they were left outdoor for 100 days and showed no viscosity change and hue degradation even if they were exposed to a high temperature under the presence of air.

TABLE 7

|  | EXAMPLES | | | COMP. EXAMPLES | |
| --- | --- | --- | --- | --- | --- |
|  | Z-1 Trial Pro. A | Z-2 Trial Pro. B | Z-3 Trial Pro. C | Z-1 Comp. Oil A | Z-2 Comp. Oil B |
| COS test (230° C. × 72 Hr) | | | | | |
| Viscosity change (%) | 0.1 | 0.1 | 0.1 | 0.3 | 0.5 |
| Change of TAN (mg KOH/g) | 0.0 | 0.0 | 0.0 | 0.2 | 0.2 |
| Weight change of metal piece | Passed | Passed | Passed | Passed | Passed |
| Amount of sludge (mg/100 ml) | 0.0 | 0.0 | 0.0 | 0.0 | 0.0 |
| Weather resistance test (Outdoor temperature × outdoor leaving for 100 days) | | | | | |
| Before test (ASTM color) | L0.5 | L0.5 | L0.5 | L0.5 | L0.5 |
| After test (ASTM color) | L0.5 | L0.5 | L0.5 | L1.5 | L1.5 |

Comparative Example Z-1

To a four-necked flask of 2 liter inner volume equipped with a water measuring tube, a cooling tube and a stirrer, 500 ml of N-methyl-2-pyrrolidone was charged, 770 g (7 mol) of thiophenol and 392.7 g (7 mol) of potassium hydroxide were added and, further, 511 g (3.5 mol) of m-dichlorobenzene was added and stirred. They were heated in an oil bath till 170° C. and the contents were separated by a water measuring tube into two layers, that is, an upper layer consisting of water and a lower layer consisting of N-methyl-2-pyrrolidone and m-dichlorobenzene, from which 126 g of water was removed.

After cooling the contents to a room temperature, 70 g of cuprous chloride was added. Then, they were heated at 210° C., reacted at that temperature for 10 hours under stirring and filtered after the reaction was over. The liquid filtrate was subjected to atmospheric distillation at 180° C. to 210° C. and unreacted thiophenol, m-dichlorobenzene and N-methyl-2-pyrrolidone were removed. Then, 617 g of a fraction at 220° C.–230° C./5 Torr was obtained as m-bis (phenylmercapto)benzene (m-3P2T) by vacuum distillation. The yield of m-bis(phenylmercapto) benzene (m-3P2T)

As mentioned above, a heat resistant lubricating oil composition of the present invention comprises a heat resistant base oil, a specified polyphenyl thioether and free radical chain stopper type antioxidant, which shows high heat resistance and oxidation resistance under severe working conditions, particularly, a high temperature condition of higher than 200° C. Further, as the wear-resistance of the heat resistant lubricating oil composition is excellent, it can be useful for jet engine oils, turbocharger engine oils, gas turbine oils. According to the present invention, a method of preventing oxidation using a polyphenyl thioether, which contributes to the improvement of heat resistance and oxidation resistance of a heat resistant base oil.

Further, a method for producing a polyphenyl thioether includes a step of purifying treatment, which can provide a commercially valuable polyphenyl thioether excellent in the weather resistance and hue stability.

What is claimed is:

1. A lubricating oil composition, comprising:
    a lubricating base oil which is selected from the group consisting of
        (i) a polyol ester, and
        (ii) an admixture of a polyphenylether and a polyol ester, wherein said polyol ester is an ester of a hindered alcohol having 5 to 30 carbon atoms and an aliphatic acid which is a linear or branched aliphatic acid of 4 to 10 carbon atoms; and wherein said polyphenylether is a compound which contains 3 to 6 aromatic rings, in which each aromatic ring is bonded to another via an oxygen atom; and from 0.05% by weight to 10% by weight, based on the total weight of the lubricating oil composition, of a polyphenyl thioether represented by formula (I) as follows:

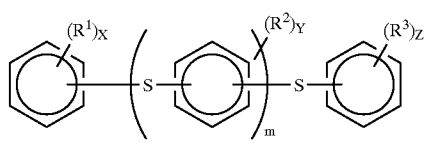
[I]

where $R^1$, $R^2$, and $R^3$ may be identical or different and each represents a hydrogen atom or a hydrocarbon group of 1 to 24 carbon atoms, and x, y and z may be identical or different and each represents an integer from 1 to 4, and m represents an integer from 1 to 3.

2. The lubricating oil composition as defined in claim 1, wherein the polyphenyl thioether is a compound represented by the following formula {II}:

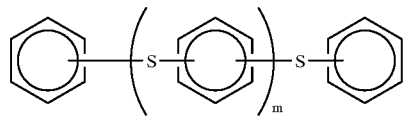
[II]

where m is an integer from 1 to 3.

3. The lubricating oil composition of claim 2, wherein the polyphenyl thioether has thioether bonding positions at meta-positions.

4. The lubricating oil composition of claim 1, which further comprises an antioxidant which is a diarylamine or a hindered phenol.

5. The lubricating oil composition of claim which further comprises an anti-wear additive which is selected from the group consisting of 0.1–10% by weight of a phosphate ester compound represented by the general formula {V}:

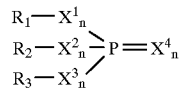

and an amine salt of such compound in which $R_1$ to $R_3$ which may be identical or different, each is a hydrogen atom or a hydrocarbon group of 1 to 18 carbon atoms; and $X^1$–$X^4$ each represent an oxygen atom or a sulfur atom and n each is independently 0 or 1.

6. The lubricating oil composition of claim 1, wherein the polyol ester is an ester of a pentaerythritol and an aliphatic acid of 4 to 12 carbon atoms.

* * * * *